United States Patent [19]
Grodzins et al.

[11] Patent Number: 6,081,580
[45] Date of Patent: *Jun. 27, 2000

[54] TOMOGRAPHIC INSPECTION SYSTEM

[75] Inventors: Lee Grodzins, Lexington, Mass.; William L. Adams, Powell, Ohio

[73] Assignee: American Science and Engineering, Inc., Billerica, Mass.

[*] Notice: This patent issued on a continued prosecution application filed under 37 CFR 1.53(d), and is subject to the twenty year patent term provisions of 35 U.S.C. 154(a)(2).

[21] Appl. No.: 09/149,204

[22] Filed: Sep. 8, 1998

Related U.S. Application Data
[60] Provisional application No. 60/059,787, Sep. 9, 1997.

[51] Int. Cl.[7] .................................................. G01N 23/201
[52] U.S. Cl. .............................. 378/87; 378/89; 378/54; 378/57
[58] Field of Search .............................. 378/87, 86, 70, 378/76, 88, 89, 57, 53, 54, 95

[56] References Cited

U.S. PATENT DOCUMENTS

| | | | |
|---|---|---|---|
| 4,064,440 | 12/1977 | Roder | 378/52 |
| 4,870,670 | 9/1989 | Geus | 378/87 |
| 5,179,581 | 1/1993 | Annis | 378/57 |
| 5,247,561 | 9/1993 | Kotowski | 378/87 |

FOREIGN PATENT DOCUMENTS 0 261 984 A2   9/1987   European Pat. Off. .

*Primary Examiner*—Drew A. Dunn
*Assistant Examiner*—Michael J. Schwartz
*Attorney, Agent, or Firm*—Bromberg & Sunstein LLP

[57] ABSTRACT

A tomography system for analyzing an object concealed within an enveloping surface. The system has multiple beams of penetrating radiation, each beam disposed with a distinct orientation with respect to the enveloping surface. Detectors are provided for measuring radiation backscattered by the contents of the enveloping surface and for measuring radiation transmitted through the enveloping surface. The enveloping surface is moved with respect to the multiple beams, and a timer provides for measurement of a time difference between the appearance of features in signals of respective detectors, allowing geometrical characteristics of the features to be determined and displayed.

13 Claims, 3 Drawing Sheets

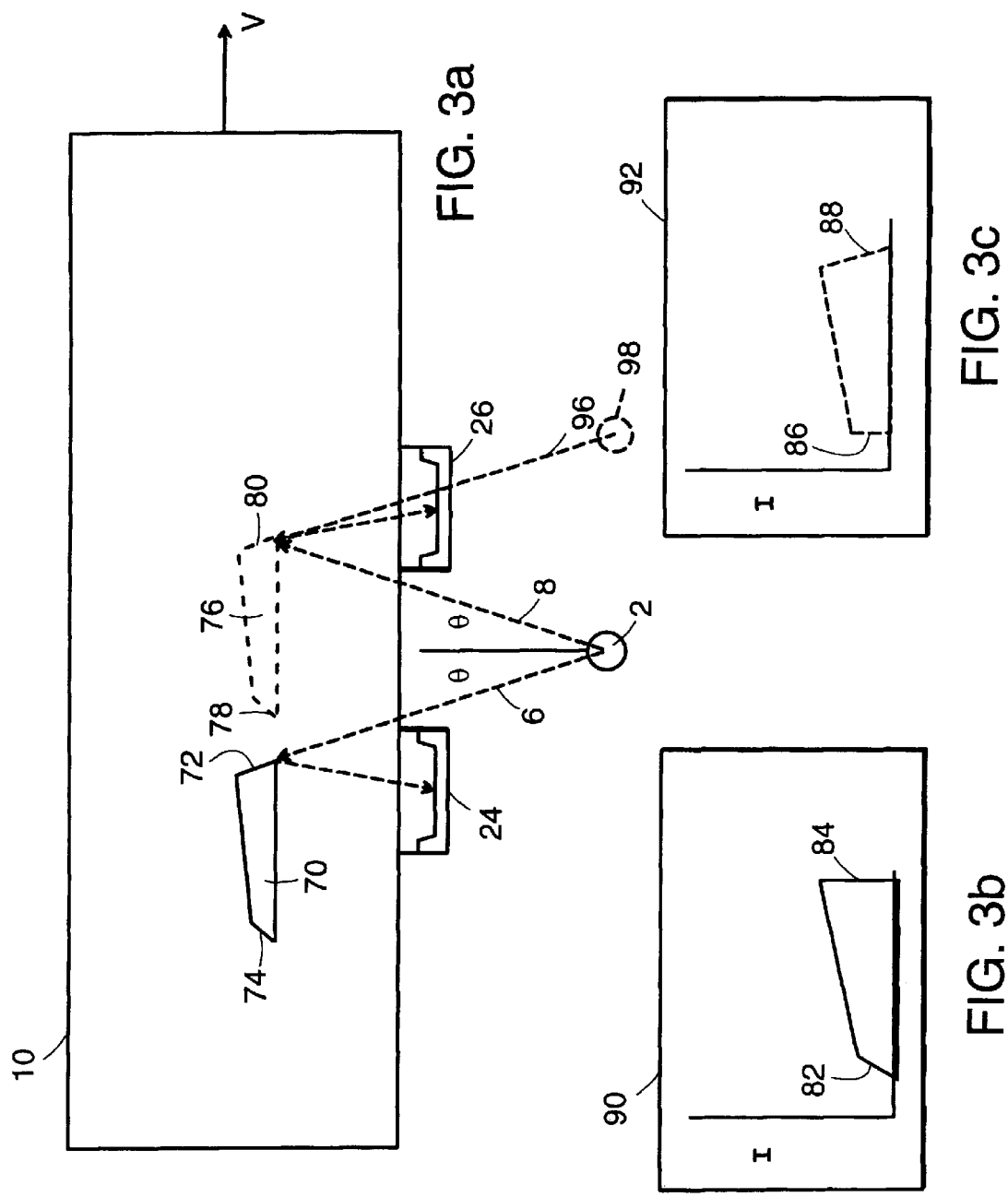

TOMOGRAPHIC INSPECTION SYSTEM

The present application claims priority from U.S. provisional application Ser. No. 60/059,787 filed Sep. 9, 1997, which application is herein incorporated by reference.

TECHNICAL FIELD

The present invention relates to x-ray inspection of containers, and, more particularly, to x-ray inspection employing the detection of backscatter radiation by means of multiple backscatter detectors in order to derive spatial and material information with respect to sources of scattering.

1. Background of the Invention

It is desirable to be able to determine the presence of objects, such as contraband, weapons, or explosives, that have been concealed in an enclosure, such as luggage or a shipping container. Conventional x-ray techniques provide measures either of attenuation, in the case of transmission techniques, or of scatter, in the case of scatter techniques, but, in both cases, the measures are effectively integrated over the line-of-sight of the respective transmission or scatter detectors. Thus, the image obtained is substantially a two-dimensional image, or, stated another way, the image is a projection of the volumetric information onto the plane of the detectors.

2. Summary of the Invention

In accordance with one aspect of the invention, in one of its embodiments, there is provided a tomography system for analyzing an object concealed within an enveloping surface. The system has at least one source of penetrating radiation for emitting a plurality of beams, each beam emitted along, a beam axis disposed with an orientation with respect to the enveloping surface such that the orientations of respective beams are distinct. Additionally, the system has a plurality of scatter detectors for detecting penetrating radiation scattered by a feature of the object and for generating signals, and a scanning arrangement for moving the enveloping surface in a direction of motion with respect to the at least one source of penetrating radiation, and a timer for comparing the time penetrating radiation scattered by the feature of the object is detected by each of the plurality of scatter detectors.

In accordance with an alternate embodiment of the invention, the tomography system may also have a controller for processing the signals and determining a position in three-dimensional space of the feature of the object. The tomography system may also have one or more transmission detectors for detecting radiation traversing the enveloping surface in a direction perpendicular to the direction of motion of the enveloping surface. The source of penetrating radiation may be an x-ray source, and two beams of penetrating radiation may be incident upon the enveloping surface at angles disposed on both sides of the normal to the direction of motion of the enveloping surface in a plane parallel to the plane of motion of the enveloping surface. The tomography system, in accordance with yet another alternate embodiment of the invention, may have a conveyor for transporting the enveloping surface.

In accordance with another aspect of the present invention, there is provided a method for determining the depth of a feature from an edge of an enveloping surface undergoing motion at a constant velocity. The method consists of the steps of a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the feature with a plurality of scatter detectors;

c. comparing the time penetrating radiation scattered by the feature is detected by respective detectors for establishing a time difference;

d. determining a distance from the vertex to the feature on the basis of the time difference;

e. measuring a distance from the vertex to the edge of the enveloping surface; and f. calculating the depth of the feature from the edge of the enveloping surface.

In accordance with an alternate embodiment of the invention, a method is provided for determining the relative depth of first and second features in an enveloping surface undergoing motion at a constant velocity where distances are determined with respect to the point of intersection of the respective beam axes.

In accordance with yet other aspects of the present invention, methods are provided for producing a three-dimensional image of an object within an enveloping surface where the enveloping surface is undergoing motion at a constant velocity, displaying a stereographic display of the contents of the enveloping surface, and determining a density of the object.

BRIEF DESCRIPTION OF THE DRAWINGS

The foregoing features of the invention will be more readily understood by reference to the following detailed description taken with the accompanying drawings in which:

FIGS. 3a–3c illustrate the application of the stereographic imaging system of FIG. 1 for deriving geometrical information regarding a concealed object.

DETAILED DESCRIPTION OF PREFERRED EMBODIMENTS

Figure 1:
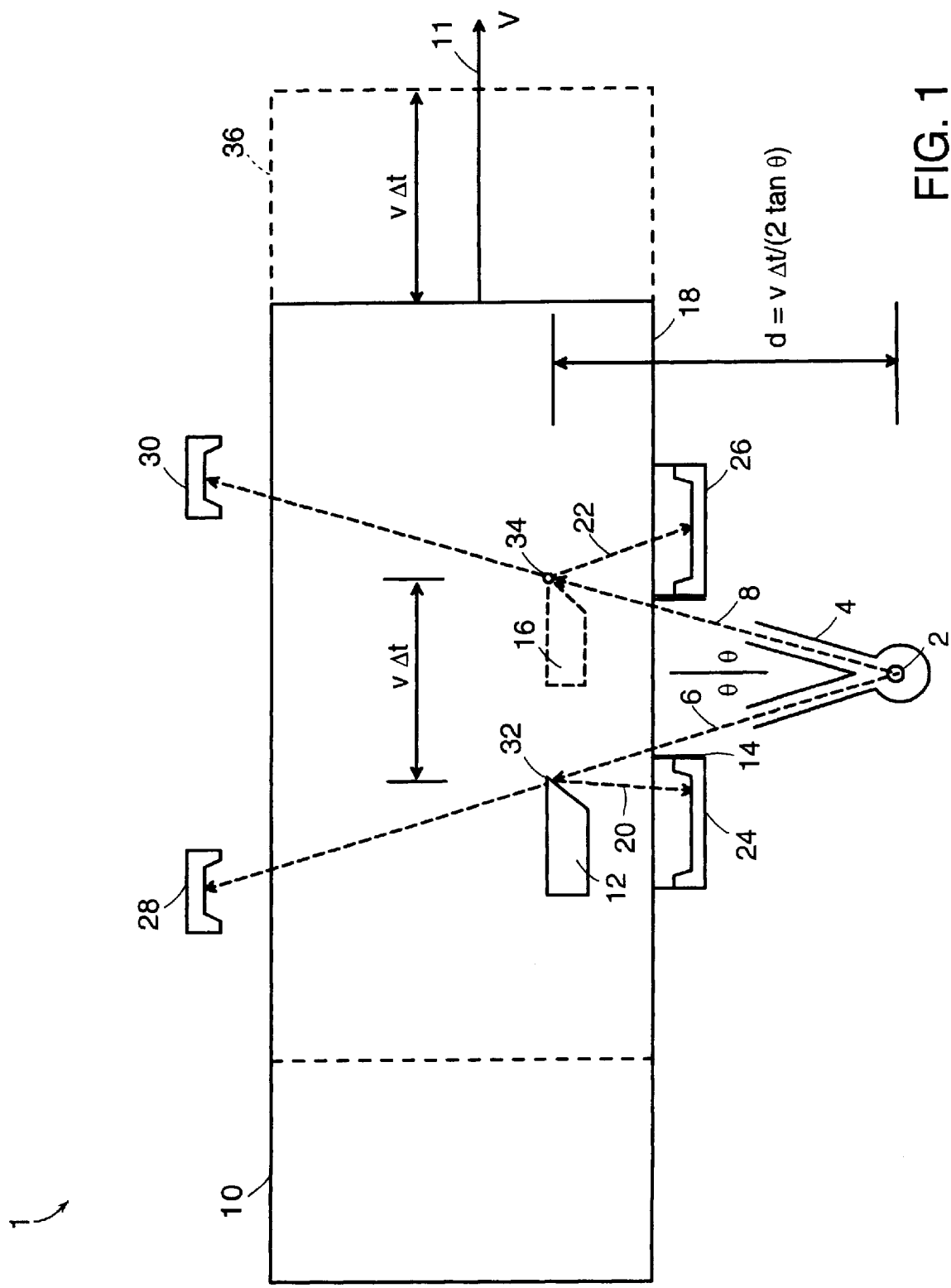
FIG. 1 provides a schematic representation of a stereographic imaging system showing a plurality of x-ray beams incident upon an enclosure and multiple detectors in accordance with a preferred embodiment of the present invention.

Referring first to FIG. 1, a schematic view is shown of the elements of a stereographic x-ray inspection system, designated generally by numeral 1. A source 2 emits penetrating radiation through a collimator slit 4 so as to form two beams 6 and 8 of predetermined cross section such as a pencil beam or a fan beam, for example. Other structures employed in the formation of beams of predetermined cross section are within the scope of the invention as herein described and of the appended claims. Beams 6 and 8 of penetrating radiation, may, for example, be beams of x-rays of various energies such as are suited to the particular application. Source 2 of penetrating radiation may be an x-ray tube, for example. The application of multiple beams as taught in this description is within the scope of the invention without regard to the methods for generating the beams. Beams 6 and 8 will be referred to in the present description, without limitation, as x-ray beams, and further as a pencil beams, again, without limitation. Beams 6 and 8 are allowed to pass through a container 10, which is moving, with respect to beams 6 and 8 in a direction 11, here indicated, without limitation, as a rightward direction, with a velocity designated V. The motion is relative, such that either container 10 or source 2 may be in motion. Beams 6 and 8 are disposed at angles, one on each side of the normal to the direction of motion of container 10 in the plane of the paper. Without loss of generality and for illustrative purposes only, the angles are shown to be equal and are designated θ, such that beams 6 and 8 are thus separated with respect to one another by an angle 2θ. The penetrating radiation 20 scattered backward from object 12 is detected by backscatter detector 24 which may be one of many forms of x-ray detector or counter known to persons skilled in the art of x-ray detection. Similarly, the penetrating radiation 22 scattered backward from object 16 is detected by backscatter detector 26. Detectors 24 and 26 may have collimators 14 for limiting the viewing angles of the respective detectors.

In addition to scatter detectors 24 and 26, one or more transmission detectors 28 and 30 may be provided for detecting the intensity of beams 6 and 8, respectively, that have traversed container 10.

Distance d from source 2 to an object in the direction perpendicular to the direction of motion 11 can be determined since velocity of motion v and angles θ are known. Detector 24 begins to detect radiation scattered by object 12 at a time t when leading point 32 just intercepts beam 6. At a later time, t+Δt, the same leading point (now designated by numeral 34) of the same object (now designated by numeral 16) intercepts beam 8. Object 12 has traversed a distance v Δt. Perpendicular distance d from source 2 to object point 32 (or 34) is then uniquely determined by the relation: d=v Δt/[2 tan θ].

The information regarding distance d is advantageous for determining an accurate measure of the average atomic number characterizing object 12. Determination of the average atomic number characterizing object 12 is often a principal reason for performing the described backscatter measurements. More particularly, the intensity of x-rays backscattered from an object depends on five factors:
I=f·g·h·k·ε, where

- f is the geometrical efficiency faction and equals the product of the source-to-feature solid angle Ω (source-to-feature) and the feature-to-detector solid angle Ω (feature-to-detector);
- g is the principal atomic number dependence on the mass absorption coefficients μ; in particular, for scattering through π radians, g=μ(scattering)/[μ(total in)+μ(total out)];
- h is the dependence on the thickness D of the feature, $$h = 1 - e^{[\mu(total\ in) + \mu(total\ out)D]};$$

- k is the dependence on intervening material of thickness b and absorption μ, $$k = e^{[-\mu b(in) - \mu b(out)]};$$

and
- ε is the known intrinsic efficiency of the detector for the detected radiation.

Knowledge of the distances of the features can be used to get a measure of factors f, h, and k, so that the factor g, which is strongly dependent on the mean atomic number of the material can be accurately measured. The analysis proceeds by first analyzing objects closest to the source-detector, then the next closest, and so on, recursively.

The closest object has little, if any, intervening material so that the factor k can be neglected. The factor h is, in practice, only significant for objects thin in the beam direction; h is close to unity for objects more than a centimeter thick. A measure of thickness is determined by methods in accordance with this invention, advantageously increasing the reliability of determinations. The largest uncertainty to knowing the mean atomic number is typically the geometrical efficiency factor f which depends strongly on the position of the object. The determination of that position by the methods described herein results in a reliable determination of the factor g which, in turn, gives the measure of the mean atomic number of the material. Knowledge of the thickness and atomic number of the closest object 40 (shown in FIG. 2) can then be used to determine the factor k when analyzing a deeper object 44 (shown in FIG. 2).

Figure 2:
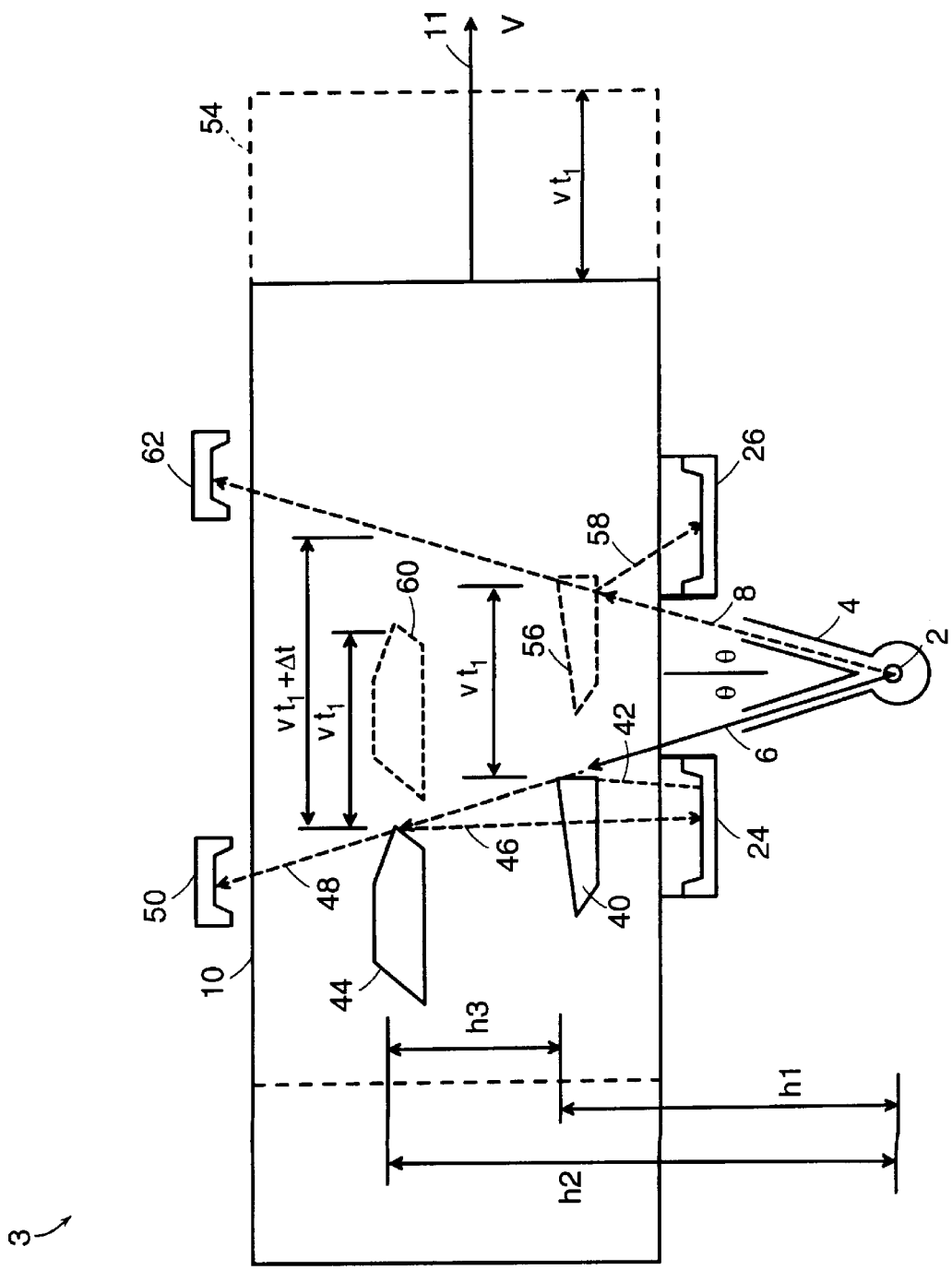
FIG. 2 illustrates the application of the stereographic imaging system of FIG. 1 for providing information regarding the position in three-dimensions of features of objects within an enclosure.

Referring now to FIG. 2, a method of finding distances, in accordance with a preferred embodiment of the present invention, is now described in relation to two objects 40 and 44. Objects 40 and 44 are disposed such that they intercept beam 6 simultaneously, as enclosure 10 is moved in direction 11 at speed v. Transmitted beam 48, detected in transmission detector 50, also intercepts both objects simultaneously. The transmitted intensity measured by detector 50 is insensitive to both the relative and absolute positions of objects 40 and 44. To measure these positions, the time difference is measured between the absorption signals for each object in the two transmission detectors 50 and 62. The difference in time signals determines the distances on the basis of geometrical considerations similar to those described above with respect to the backscatter detectors. Transmission detectors 50 and 62, however, measure the projected absorption due to all objects traversed by x-ray beams 6 and 8, and the signals may be insensitive to smaller, lighter objects. The backscatter signals, on the other hand, are especially sensitive to objects on the side of the container nearest the backscatter detectors 24 and 26. When container 10 has moved a distance v $t_1$, the object 40, now labeled as 56, intercepts beam 8. Object 44 is now in position 60 and will not intercept beam 8 until a time Δt later. The time difference Δt is a direct measure of distance h3 between objects 40 and 44: h3=v Δt/[2 tan θ].

Depth information, such as distances h1 and h2 may be determined automatically using correlation techniques, as known to persons skilled in the art, wherein an image created by each beam, described in digital form, such as in a wavelet representation, for example, is correlated with the image derived from another beam for determining time differences between any two correlated points from the two images. Correlation of the two images allows the formation of a three-dimensional image for display and viewing.

It is not necessary that beams 6 and 8 share an actual common origin, and an effective vertex may be understood to exist where beam axes 6 and 8 intersect. The beams may also be skew, within the scope of the invention, with a known offset and with an effective vertex determinable in a projection plane. The measurement of time differences by means of timers of any sort is well known in the instrumentation arts and any method employed for measurement of such time differences is considered within the scope of this invention and of the appended claims. It should be appreciated that the time differences are tantamount to spatial distances on the recorded images of objects in the views obtained by the two detectors.

The location in three dimensions of the boundaries of objects concealed within a container may be further enhanced by application of a further embodiment described now with reference to FIG. 3a. An object 70 is shown with a shape in which the leading edge 72 is parallel to beam 6 while anterior edge 74 is parallel to beam 8. The intensity distribution in detector 24 is depicted as plot 90 in FIG. 3b. Leading edge 72 shows up as a dingle intensity 84; there is no evidence of a slope in object 70. Trailing edge 74, however, produces a trailing intensity 82. When object 70 crosses beam 8, the scattered intensity has a very different intensity distribution, as shown in plot 92 of FIG. 3c. Now, leading edge 80 becomes a sloping intensity 88, while trailing edge 78 is a single point, showing no indication of the actual shape. Thus, the intensity patterns, 90 and 92, corresponding to the signals of the two detectors 24 and 26, can be combined to reveal information about the topology of object 70.

The use of two angle x-ray beams may also advantageously allow a three-dimensional image to be visualized. The method, in accordance with an alternate embodiment of the invention, is described with reference to FIGS. 3a–3c. The two images, represented by the one-dimensional slices shown in plots 90 and 92, viewed independently by methods well known in the art, such as red-green colored or orthogonally polarized light, can be superposed to produce a three-dimensional image of the contents of the container as determined by backscattered radiation. The image is similar to the 3-D image produced by binocular vision since the image obtained with beam 6, when displaced to a position such as 98, acts as if it were beam 96. When the two images from beam 8 and 98 are superposed, the classic geometry of binocular 3-D imaging results.

By employing flying spot scanning beams or by segmenting detectors 24 and 26 with respect to displacement along the direction out of the plane of the paper, the same information is available for each plane parallel to the plane of the paper. Thus, using well-known tomographic principles, the entire volumetric structure of object 41 and of every object concealed within container 10 may be reconstructed.

It should be noted that while the above procedures have been explained in terms of objects with well-defined shapes and sizes, in practice, however, the method may be used to reconstruct images of objects and to display them in pseudo three dimensional form using well-known vanishing point or other appropriate projection.

It is not necessary, in practicing the method taught by the invention, to process, in the manner described, the entire volume of a container. The invention may be used with edge enhancement routines to define the specific edges which are to be located in space. In this way, the edges of an image of an object may be projected in pseudo 3-D with the edges enhanced.

In an alternate embodiment of the invention, step discontinuities in the detected scatter intensity due to the passage of object edges through the respective x-ray beams may be noted, either by recording the magnitude of the step discontinuities or by known thresholding techniques. By noting the temporal correspondence between discontinuities observed in left and right beams, the three-dimensional position of the point of transition as well as the intensity of either the high or low intensity at the transition may be stored in a four-dimensional matrix which corresponds to a generalized image. The four-dimensional matrix contains sufficient information to reconstruct, using algorithms known to persons skilled in the art of image processing, either a pseudo three-dimensional or stereographic pair which may be used to display an image of the scanned object.

Additional information may also be obtained from the measurements hereabove described. For example, information contained in the transmission beam 27 (shown in FIG. 1) may be used to determine the density of observed objects, since their size and shape are known, as described, and the total mass absorption in the path of the transmission beam is determinable from the attenuation of the transmission beam. Thus the entire mass contained within an object, and thus the approximate density may be calculated.

It should be noted that the described embodiments of the invention may be used in combination of two or more of the above embodiments in order to inspect the contents of the container. The described embodiments of the invention are intended to be merely exemplary and numerous variations and modifications will be apparent to those skilled in the art. All such variations and modifications are intended to be within the scope of the present invention as defined in the appended claims.

We claim:

1. A tomography system for analyzing an object concealed within an enveloping surface, the system comprising:
   a. at least one source of penetrating radiation for emitting a plurality of beams, each beam emitted along a beam axis disposed with an orientation with respect to the enveloping surface such that the orientations of respective beams are distinct;
   b. a plurality of scatter detectors for detecting, at distinct times, penetrating radiation scattered by a feature of the object and for generating signals;
   c. a scanning arrangement for moving the enveloping surface in a direction of motion with respect to the at least one source of penetrating radiation; and
   d. a timer for comparing the times at which penetrating radiation scattered by the feature of the object is detected by the plurality of scatter detectors.

2. The tomography system in accordance with claim 1, additionally comprising a controller for processing said signals and determining a position in three-dimensional space of the feature of the object.

3. The tomography system in accordance with claim 1, additionally comprising a transmission detector for detecting radiation traversing the enveloping surface in a direction perpendicular to the direction of motion of the enveloping surface.

4. The tomography system in accordance with claim 1, wherein the source of penetrating radiation is an x-ray source.

5. The tomography system in accordance with claim 1, wherein two beams of penetrating radiation are incident upon the enveloping surface at angles disposed on opposite sides measured from the normal to the direction of motion of the enveloping surface in a plane parallel to the plane of motion of the enveloping surface.

6. The tomography system in accordance with claim 1, additionally comprising a conveyor for transporting the enveloping surface.

7. A method for determining the depth of a feature from an edge of an enveloping surface undergoing motion at a constant velocity, the method comprising:
   a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the feature with a plurality of scatter detectors;

c. comparing the time penetrating radiation scattered by the feature is detected by respective detectors to establish a time difference;

d. determining a distance from the vertex to the feature on the basis of the time difference penetrating radiation scattered by the feature is detected by respective detectors;

e. measuring a distance from the vertex to the edge of the enveloping surface; and f. calculating the depth of the feature from the edge of the enveloping surface.

8. A method for calculating a mean atomic number characterizing a feature interior to an enveloping surface undergoing motion at a constant velocity, the method comprising:

a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the feature with a plurality of scatter detectors;

c. comparing the time penetrating radiation scattered by the feature is detected by respective detectors to establish a time difference;

d. determining a distance from the vertex to the feature and a distance from the feature to each detector on the basis of the time difference;

e. calculating a geometrical efficiency of detection based on the distance of the feature from the vertex and the distances of the feature from the respective detectors; and f. calculating a mean atomic number characterizing the feature based on the intensity of the backscattered signal from the feature and the geometrical efficiency of detection.

9. A method for determining the relative depth of first and second features in an enveloping surface undergoing motion at a constant velocity, the method comprising:

a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the first and second features with a plurality of scatter detectors;

c. comparing the time penetrating radiation scattered by the first and second features is detected by respective detectors for determining a time difference;

d. determining a first distance from the vertex to the first feature and a second distance from the vertex to the second feature on the basis of the time difference; and e. calculating the relative depth of the first and second features.

10. A method for producing a three-dimensional image of an object having edges, the object contained within an enveloping surface having contents, the enveloping surface undergoing motion at a constant velocity, the method comprising:

a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the edges of the object with a plurality of scatter detectors;

c. comparing the time penetrating radiation scattered by the edges of the object is detected by respective detectors for determining a time difference;

d. determining distances from the vertex to the edges of the object on the basis of the time difference; and e. reconstructing the shape of the object based on the determined distances.

11. A method according to claim 10, further comprising displaying a stereographic display of the contents of the enveloping surface.

12. A method for producing a three-dimensional image of objects having edges contained within an enveloping surface having contents, the enveloping surface undergoing motion at a constant velocity, the method comprising:

a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the edges of the objects with a plurality of scatter detectors;

c. creating backscatter images corresponding to each incident beam;

d. correlating the backscatter images for creating correlated set of points, lines, and objects;

e. determining the depth of each point, line and object on the basis of the correlated set of points, lines, and objects; and f. composing a three-dimensional image of the contents of the enveloping surface based on the depth of each point, line, and object.

13. A method for determining the density of an object having edges, the object contained within an enveloping surface having contents, the enveloping surface undergoing motion at a constant velocity, the method comprising:

a. illuminating the enveloping surface with a pair of beams of penetrating radiation, each beam incident on the enveloping surface along a beam axis disposed with an orientation with respect to the motion of the enveloping surface such that the orientations of respective beams are distinct, the pair of beams having a vertex;

b. detecting penetrating radiation scattered by the edges of the object with a plurality of scatter detectors;

c. detecting penetrating radiation transmitted in each beam through the enveloping surface for creating a measure of absorption of each beam;

d. comparing the time penetrating radiation scattered by the edges of the object is detected by respective detectors for determining a time difference;

e. determining distances from the vertex to the edges of the object on the basis of the time difference;

f. reconstructing the shape of the object based on the determined distances; and g. calculating the density of the object based on the shape of the object and the measure of absorption of each beam.

* * * * *